United States Patent
Tyvoll et al.

(10) Patent No.: US 8,481,323 B2
(45) Date of Patent: Jul. 9, 2013

(54) SYSTEMS AND METHODS FOR MEASURING GLYCATED HEMOGLOBIN

(75) Inventors: David A. Tyvoll, La Jolla, CA (US); Bryan J. Johnson, San Diego, CA (US); Kevin F. Peters, Corvallis, OR (US)

(73) Assignee: Hewlett-Packard Development Company, L.P., Houston, TX (US)

(*) Notice: Subject to any disclaimer, the term of this patent is extended or adjusted under 35 U.S.C. 154(b) by 1711 days.

(21) Appl. No.: 11/261,741

(22) Filed: Oct. 28, 2005

(65) Prior Publication Data
US 2007/0099301 A1    May 3, 2007

(51) Int. Cl.
*G01N 33/72* (2006.01)
*G01N 33/80* (2006.01)

(52) U.S. Cl.
USPC .......... 436/57; 436/63; 436/50; 422/72; 422/102; 210/515; 210/516

(58) Field of Classification Search
USPC ..... 436/67, 63, 50; 422/99, 72, 102; 210/515, 210/516
See application file for complete search history.

(56) References Cited

U.S. PATENT DOCUMENTS

| | | | |
|---|---|---|---|
| 4,835,097 A | 5/1989 | Saunders | |
| 5,384,239 A | 1/1995 | Saunders | |
| 5,550,060 A * | 8/1996 | Saunders et al. | 436/63 |
| 5,837,546 A | 11/1998 | Allen et al. | |
| 5,932,480 A | 8/1999 | Maruo et al. | |
| 5,968,839 A | 10/1999 | Blatt et al. | |
| 6,174,734 B1 | 1/2001 | Ito et al. | |
| 6,316,265 B1 | 11/2001 | Lee et al. | |
| 6,399,293 B1 | 6/2002 | Pachl et al. | |
| 6,582,964 B1 | 6/2003 | Samsoondar et al. | |
| 6,818,416 B2 | 11/2004 | Pachl et al. | |
| 2003/0129665 A1* | 7/2003 | Selvan et al. | 435/7.2 |
| 2007/0267361 A1* | 11/2007 | Tyvoll et al. | 210/787 |

OTHER PUBLICATIONS

Gifford, S.C., Frank, M.G., Derganc, J., Gabel, C., Austin, R.H., Yoshida, T.,& Bitensky, M.W..(2003). Parallel Microchannel-Based Measurements of Individual Erythrocyte Areas and Volumes. Biophysical Journal, 84, 623-633.*

Figdor, Carl, G. "Isolation of Functionally Different Human Monocytes by Counterflow Centrifugation Elutriation", Blood, vol. 60, No. 1Jul. 1982.*

Saunders A M: "Retrospective time-resolved testing: model I—time-resolved glycohemoglobin." Clinical Chemistry Sep. 1991, vol. 37, No. 9, pp. 1531-1533.

(Continued)

*Primary Examiner* — Krishnan S Menon
*Assistant Examiner* — Rebecca M Fritchman

(57) ABSTRACT

The present invention is drawn to a method of measuring glycated hemoglobin, which can comprise steps of establishing multiple age-specific groups of red blood cells, and measuring $HbA_{1c}$ levels of at least one of said groups. In another embodiment, a system for measuring glycated hemoglobin can comprise a separating device configured to separate red blood cells into multiple age-specific groups, and a measuring device configured to measure $HbA_{1c}$ levels of at least one of said groups.

30 Claims, 4 Drawing Sheets

OTHER PUBLICATIONS

Nakashima K et al.: "Glycated hemoglobin in fractionated erythrocytes." Clinical Chemistry Jun. 1989, vol. 35, No. 6, pp. 958-962.

Lasch J et al.: "Separation of erythrocytes into age-related fractions by density or size? Counterflow centrifugation." CCLM/FESCC Jul. 2000, vol. 38, No. 7, pp. 629-632.

Fitzgibbons J F et al.:"Red cell age-related changes of hemoglobins Ala+b and Alc in normal and diabetic subjects." Journ. Clini. Invest. Oct. 1976, vol. 58, No. 4, pp. 820-824.

Int'l Search Rep & Writt Opinion from PCT/US2006/041502, dated Feb. 7, 2007.

Gifford, Sean C., "Parallel Microchannel-Based Measurements of Individual Erythrocyte Areas and Volumes", Biophysical Journal, vol. 84, Jan. 2003, pp. 623-633.

Stivers, Carole R., "A Miniaturized Self-Contained Single-Use Disposable Quantitative Test for Hemoglobin Al c in Blood at the Point of Care", Diabetes Technology & Therapeutics, vol. 2, No. 4, 2000.

Professional-Use Product Insert for Al c Now, manufactured by Metrika, 90067 rev B, 1988.

Medical Devices Agency Evaluation Report, MDA 02098, 2003.

\* cited by examiner

SYSTEMS AND METHODS FOR MEASURING GLYCATED HEMOGLOBIN

BACKGROUND OF THE INVENTION

Red blood cells (RBC), or erythrocytes, are responsible for the transport of oxygen throughout the body. Specifically, hemoglobin, which is part of a healthy red blood cell, is an iron-containing respiratory macromolecule which functions in its oxygenated form to carry oxygen from the lungs to tissue sites. As is known, red blood cells have a membrane that is freely permeable to glucose. When glucose or other sugar moieties enters a red blood cell, glycated hemoglobin (GHb) can be formed. Glycated hemoglobin refers to various hemoglobin derivatives formed by covalent attachment of sugar moieties, in particular glucose. The amount of glycated hemoglobin is related to glucose concentration in the blood, as well as the duration of exposure to glucose. The common index of glycated hemoglobin is known as $HbA_{1c}$, and the ratio of $HbA_{1c}$ to total hemoglobin is known as % $HbA_{1c}$.

As a general matter, red blood cells have a lifetime of approximately 120 days, and the amount of glycation of hemoglobin varies as a function of the 120 day lifetime of the cell. As the reaction of glucose with hemoglobin molecules is slow and generally irreversible in vivo, the amount of glycated hemoglobin ($HbA_{1c}$) has traditionally been considered to be an accurate index of blood glucose concentrations over the previous 3-4 months. Accordingly, diabetes patients are advised to check their $HbA_{1c}$ value every 3-4 months. For example, the American Diabetes Association (ADA) recommends an $HbA_{1c}$ test about 2 to 4 times per year and further recommends an $HbA_{1c}$ of level below 7%.

The determination of total hemoglobin can be performed by simple absorbance or reflectance measurements. Typically the iron is reduced by potassium ferricyanide to create methemoglobin, which is measured at 565 nm. The determination of the amount of glycated hemoglobin can be performed by numerous methods known in the art such as by competitive or immunometric assays. In the latter, the antigens can be insolubilized on a solid phase and a labeled antibody is incubated in their presence. The antibody-antigen complex can be detected by optical or fluorescent methods. This method can be practiced on ~10 µl of blood. However, this method is carried out using a random cell sample collected from the blood, and thus, provides only a single datum of average glucose regulation history at a specific point in time. The measured average value can be skewed toward newer cells because they are more prevalent. Yet the measured average amount of glycation of hemoglobin will be understated for younger cells because of their briefer exposure to glucose than for older cells. Because of this, testing glycated hemoglobin every 3-4 months will not accurately reflect the quality of glucose regulation in some diabetic patients. For instance, a diabetic patient can be systematically under-regulating their glucose levels for 1-3 months, and then over-regulating their glucose levels during the most recent 30 days prior to the test. Because of the large influence that the newest red blood cells have on $HbA_{1c}$ testing, the average glycated hemoglobin can appear in the normal range, thus misleading the patient and the caregiver as to the quality of glucose regulation. As a result, it would be beneficial to provide a practitioner or a subject more detailed information related to patient glucose levels over shorter periods of time, as well as provide more accurate information related to compliance with respect to glucose regulation.

DETAILED DESCRIPTION OF THE PREFERRED EMBODIMENT(S)

Figure 1:
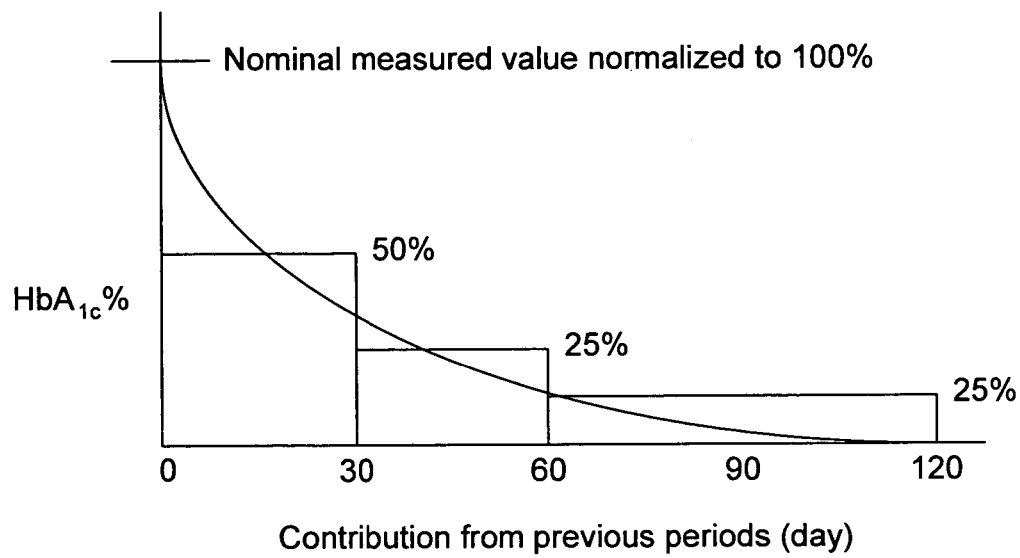
FIG. 1 is a graph depicting $HBA_{1c}$ levels as it generally relates to cell age.

Before particular embodiments of the present invention are disclosed and described, it is to be understood that this invention is not limited to the particular process and materials disclosed herein as such may vary to some degree. It is also to be understood that the terminology used herein is used for the purpose of describing particular embodiments only and is not intended to be limiting, as the scope of the present invention will be defined only by the appended claims and equivalents thereof.

In describing and claiming the present invention, the following terminology will be used:

The singular forms "a," "an," and "the" include plural referents unless the context clearly dictates otherwise.

As used herein, the terms "microfluidic coupon" or "coupon" are to be understood to refer to a device used to centrifuge and/or manipulate one or more microfluids, generally for the purposes of testing the fluid or liquid in a centrifugation test regime. Microfluidic coupons utilized in the present invention can include, but are not limited to, disk-shaped devices formed of poly(methylmethacrylate) (PMMA), acetonitrile-butadiene-styrene (ABS), polycarbonate, etc. While not so limited, such disks can be similar in appearance to well-known optical disks, e.g., compact disks (CDs). It is also understood that such materials may optionally include coatings to minimize sticking and aggregation of cells. Coatings used in the present invention can include, but are not limited to, polyethylene glycols (PEG), polysilicones and polydimethylsiloxanes (PDMS), and organic/silicone copolymers (PEG-silanes). They may also optionally include detergents and surfactants, which may be present in amounts sufficient to prevent sticking and aggregation, but insufficient to cause cell lysis, except where desired.

As used herein, the term "valve" includes both passive valves and active valves. Active valves include valves having a mechanical valving gate of some type, e.g., paraffins or waxes, optically activated materials, heat-activated valves, mechanical valves, etc., whereas passive valves are static valves with no moving parts that act as a fluid valve due primarily to its geometric configuration and/or size, e.g., microfluidic valves where fluid dynamics and/or force on fluid causes fluids to pass through microchannels, etc.

As used herein, the term "microfluidics" and "microfluid" are to be understood to refer to fluids manipulated in systems that confine the fluids within geometric channels, passages, reservoirs and other chambers having at least one dimension less than about 1 mm. Similarly, the terms "microfluidic channel," or "microchannel" are to be understood to refer to channels having at least one dimension less than about 1 mm.

As used herein, the term "centrifuge," and its related terms "centrifugation" and "centrifuged," are to be understood to refer to a process in which a liquid is subjected to centripetal forces induced by rotating a reservoir in which the liquid is stored. While the term centrifuge is generally used to refer to a process in which two or more constituents of a liquid are separated due to centripetal force, the use of the term herein is not limited to any particular degree of separation of constituents of the liquid. Thus, a liquid can be centrifuged even when it has not yet exhibited visible separation of liquid constituents.

When referring to "age-specific group(s)" of red blood cells, it is understood that not all cells with an age specific group must meet the age profile, as there will typically be cells within an age specific group that do not fit the age profile. This is because of the typically imprecise methods of separating cells by age. To the extent that perfect age segregation can be carried out, that type of separation certainly falls within the present definition. However, for practical purposes, a perfect segregation is not usually possible. Thus, the term "age-specific group(s)" merely means that the group of red blood cells statistically includes more cells within a specific age group than a sample of red blood cells taken from a random sample.

When referring to fluids such as "liquids," it is understood that not all constituents of the liquid are necessarily in liquid form. For example, blood is considered to be a liquid, even though it has solid cell constituents suspended therein.

In accordance with embodiments of the present invention, a method of measuring glycated hemoglobin can comprise steps of establishing multiple age-specific groups of red blood cells, and measuring $HbA_{1c}$ levels of at least one of said groups. In another embodiment, a system for measuring glycated hemoglobin can comprise a separating device configured to separate red blood cells into multiple age-specific groups, and a measuring device configured to measure $HbA_{1c}$ levels of at least one of these groups. In these embodiments, the % $HbA_{1c}$ can also be calculated by determining the total hemoglobin as well. This method and system provide an approach to solving a problem associated with measuring average glycated hemoglobin levels over a period of 3-4 months.

As can be seen in FIG. 1, about 50% of the $HbA_{1c}$ is provided by the red blood cells that are 30 days old or younger; about 25% of the $HbA_{1c}$ is provided by the red blood cells that are from 30 to 60 days old; and about 25% of the $HbA_{1c}$ is provided by the red blood cells that are from 60 to 120 days old. Thus, when measuring the $HbA_{1c}$ levels in a typical blood sample, a skewed picture of the overall $HbA_{1c}$ index is obtained. Thus, in accordance with embodiments of the present invention, it has been recognized that it would be desirable to obtain information about $HbA_{1c}$ levels that is red blood cell age specific, rather than obtain information about average $HbA_{1c}$ levels over a period of months. In other words, in addition to learning of $HbA_{1c}$ values in relation to unglycated hemoglobin generally in blood sample, it would be more beneficial to know the $HbA_{1c}$ levels of a blood sample in relation to discrete age groups of red blood cells from unglycated hemoglobin, providing a more accurate picture of a blood sugar history of an individual. In one specific embodiment, it would also be beneficial to carry out this analysis using a small, portable device that could be easily used and located in a home or a doctor's office. It would also be desirable if such a device could function using a minimal volume of blood, for instance less than 50 µl (approximately 1-2 drops). One or more of these desirable features can be achieved in accordance with embodiments of the present invention.

It has been recognized that separating cells based on a predetermined physical property before measuring $HbA_{1c}$ levels in blood can provide a more accurate picture regarding patient compliance over the entire life of red blood cells. In other words, as a sample of red blood cells includes both young and old blood cells, and as young blood cells contribute more extensively to $HbA_{1c}$ levels than older blood cells, by separating these cells along a gradient according to age of cells and subsequently conducting one or more $HbA_{1c}$ analyses, a more accurate and time sensitive picture of the $HbA_{1c}$ levels over a 3-4 month period can be obtained.

The segregation of red blood cells by age can be carried out using a number of techniques. One technique is counterflow centrifugation (elutriation), which separates particles of smaller diameter or size from those of larger diameter or size. For the case of red blood cells, it is known that the size dominates the balance between sedimentation and streaming. Thus, while older red blood cells are smaller and denser than young blood cells, they elute first during the centrifugation. Other techniques can rely on other chemical or physical indicators of cell age, including membrane protein ratios, and rheological properties. These latter factors may contribute to changes in the electronic properties of the cells. In particular, differences in electronic opacity (the ratio of radio frequency impedance to dc impedance) are also related to the red blood cell age. In light of this, the dielectric properties of the cells also correlate with their age, which means that they can be microscopically segregated based on their different dielectric properties. Other microscopic means, which may include the use of a microscope, to segregate the cells can rely on their density and/or mechanical/rheological properties such as elasticity and deformability. In particular, microchannel devices are known in the art which are capable of segregating a population of red blood cells based on their age. Thus, there are a number of ways of segregating red blood cells based upon their age. Such separations can be carried out in accordance with embodiments of the present invention for the purpose of determining $HbA_{1c}$ levels based on cell age. In addition, it is understood that ordinary precautions are taken to minimize conditions that lead to cell stress, since this can reduce the efficiency of the segregation. These include the use of anti-coagulants such as heparin or EDTA in a buffer, avoidance of excessive centripetal forces, avoidance of excessive temperature deviations, etc.

Figure 2:
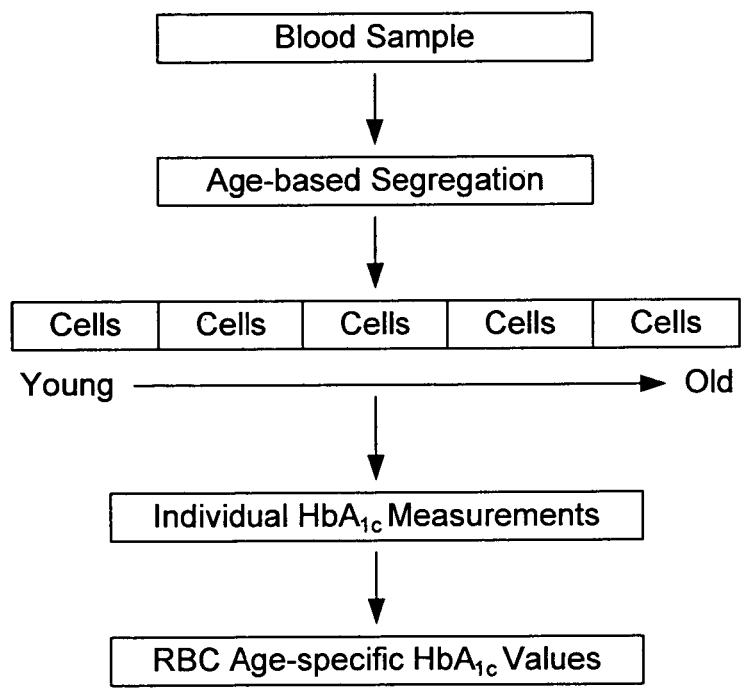
FIG. 2 graphically depicts an embodiment of a general approach to measuring $HBA_{1c}$ levels using age-based cell segregation.

A general scheme which illustrates embodiments of the present invention is shown at FIG. 2, where a blood sample is separated based on age, e.g., a gradient from young to old or vice versa. The gradient of cells can be separated by groups of cells that are statistically likely to be close in age (based on size, density, dielectric response, etc.). Each group can then be evaluated individually for $HbA_{1c}$ levels. The number of groups can be as few as two groups, e.g., cells less than 1 to 3 months old compared to cells greater than 1 to 3 months old, to as many distinct groups as a practitioner deems appropriate, e.g., from 3 to 10 or more groups. Alternatively, one or more discrete group(s) at the end or in the middle of the age gradient can be evaluated.

As mentioned above, there are different ways to segregate the cells. For illustrative purposes, several methods are described herein that utilize the size and/or density of red blood cells in order to make the separation. It should be noted that the separation is not necessarily a complete separation of groups of cells, as cells can be organized along a gradient.

Further, it is notable that when using a physical cell property to approximate age, some cells may have an age that does not fit the statistical profile of the physical property used to organize the cells along the cell gradient. However, such markers tend to be accurate, and thus, anomalies where cell age does not fit the physical profile used to separate the cells becomes less significant. Further, even if such an age-based gradient is not completely accurate, as long as the gradient provides age-related cell organization that is more age-related than a random blood sample, it is within the context of the present invention.

Figure 3:
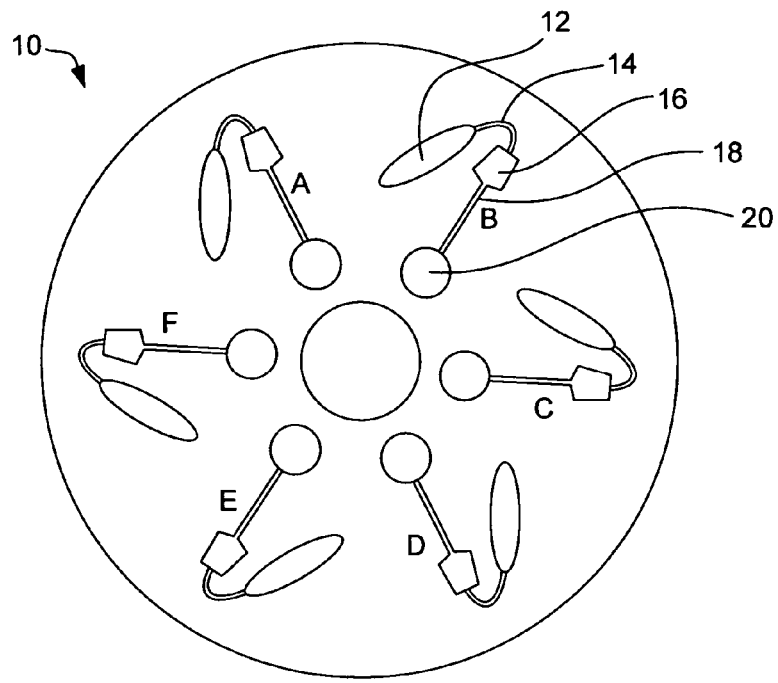
FIG. 3 is a schematic view of an exemplary microfluidic coupon in accordance with embodiments of the present invention.

This being stated, to provide more details about one specific separation method, an acceptable technique that can be used to separate red blood cells (or place cells along a cell gradient) of various sizes includes using counterflow centrifugation, or elutriation. In general, elutriation applies centrifugal force to a liquid creating a target rotational velocity sufficient to overcome capillary forces in a microfluidic system. In accordance with the present invention, the size of the microchannels is generally less than 1 mm, and is often as small as about 500 µm or less, along at least one dimension or even all dimensions. FIG. 3 depicts a microfluidic coupon 10 having an approximate shape and size of an optical disk, e.g., compact disk. This embodiment is exemplary only, as any of a number of shapes of chambers, configurations of channels, relative positioning of chambers and channels is possible, as would be known by one skilled in the art after considering the present disclosure. In FIG. 3, the microfluidic coupon includes multiple (6) fluidic separation systems A-F, each including a reservoir 12, a first microfluidic channel 14, an elutriation chamber 16, a second microchannel 18, and an analysis chamber 20 which may include vents open to the atmosphere. The reservoir can be used to receive a pure blood sample (or other red blood cell containing sample), a buffered blood sample, or a non-blood sample such as a buffer fluid. Typical buffers used for elutriation are known in the art, and include phosphate buffered saline (PBS) and derivatives thereof.

In embodiments where the reservoir contains an electrolytic buffer fluid, the red blood cells can be placed directly in the elutriation chamber. Thus, centrifugation can be used to form a gradation of red blood cells within the elutriation chamber, and electrolysis in the reservoir can be used to generate bubbles that force the gradation of red blood cells from the elutriation chamber into the second microchannel for lysing, and ultimately, to the analysis chamber. These and other embodiments are possible in accordance with embodiments of the present invention.

Figure 4A:
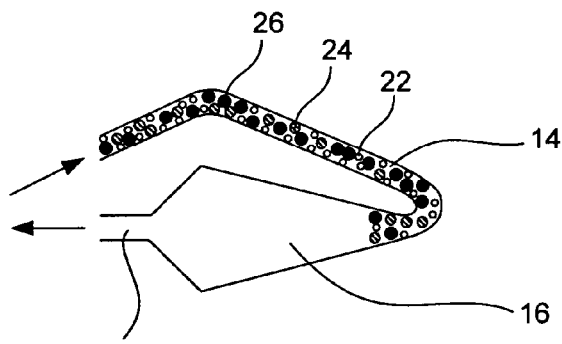
FIGS. 4A and 4B are schematic views of microchannels and an elutriation chamber used to form red blood cell gradients in accordance with an embodiment of the present invention.
Figure 4B:
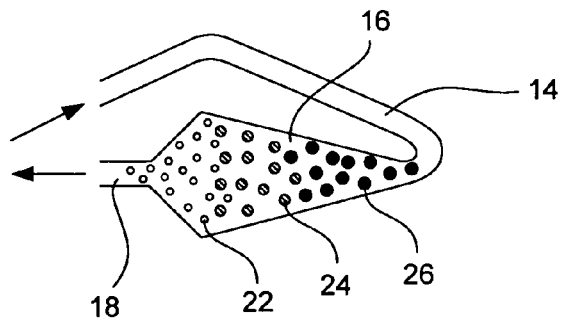

FIGS. 4A and 4B depict an alternatively shaped elutriation chamber 16 with microchannels 14 and 18. FIGS. 4A and 4B describe in greater detail the separation that occurs using a microfluidic coupon as shown in FIG. 3. Specifically, in FIG. 4A, red blood cells within various size ranges are shown as they are traveling through the first microchannel 14. The fluid movement can be caused by spinning of the microfluidic coupon. Relatively smaller-sized cells 22 (older cells), medium-sized cells 24, and larger-sized cells 26 (younger cells) are shown. As shown in FIG. 4B, as the red blood cells enter the elutriation chamber and fluid flow during spinning of the microfluidic coupon is commenced, smaller cells tend to pass further into the chamber more quickly than the larger cells, thus generating a gradation or gradient of cells based primarily on size. As suggested, in this embodiment, the counterflow can be generated by bleeding in fluid from a larger, counter-balanced reservoir, or by fluid displacement from controlled electrolysis (with voltage and current supplied via brushes and electric pads, or inductively) (not shown).

Of course, multiple reservoirs and chambers can also be configured so as to balance the overall centrifugal forces. Furthermore, multiple configurations can be used, either identical fashion (as shown in FIG. 3) or in other configurations, e.g., to generate in increasing elutriation. Increasing the flow rate from the bottom (most radially-distal) can elute the cells to form the gradient. It should be noted that the black filled larger circles represent younger cells, and the white open smaller circles represent older cells. This being stated, the size of the various cells shown in this FIG. is for graphical illustration purposes only, and should not be viewed as providing relative actual sizes of variously aged red blood cells.

Figure 5:
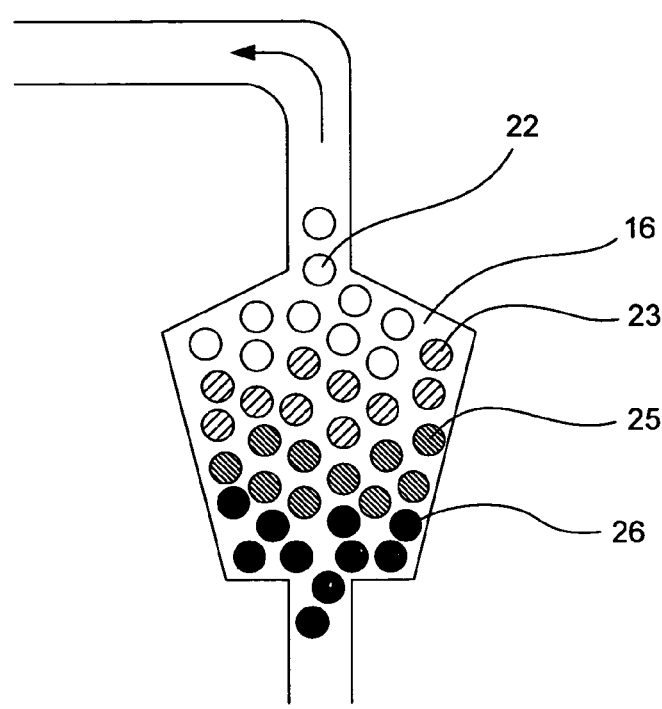
FIG. 5 is a schematic view of an alternative elutriation chamber having a red blood cell gradient contained therein in accordance with an embodiment of the present invention.

FIG. 5 depicts an elutriation chamber 16 similar to that shown in FIGS. 3, 4A, and 4B, having four groupings of cells beginning to separate or form a gradient therein, i.e. relative small cells 22, medium-small cells 23, medium-large cells 25, and larger cells 26. Again, it is notable that the cells form a gradient, and characterizing groupings of cells in four groups (or another number of groups) can be done by practitioner choice, depending on the level of detail related to $HbA_{1c}$ levels that is desired to be learned. For example, if a practitioner wants to evaluate the red blood cells that are of a particular age range, e.g., 6-8 weeks old, these cells can be placed in a group and evaluated separately.

Figure 6:
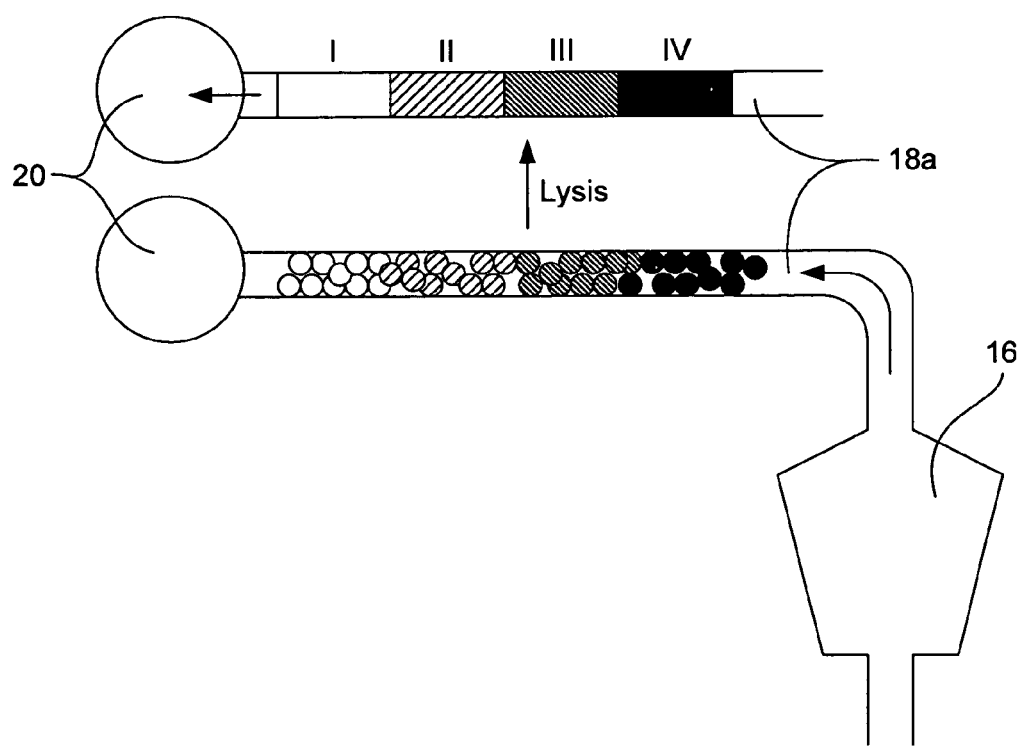
FIG. 6 is a schematic view of a system in accordance with embodiments of the present invention.

Referring to FIG. 6, once a gradient is established (or while a gradient is being established) within an elutriation chamber 16, the gradient of cells can be transferred to a lysis microchannel 18a (such as the second microchannel 18 of FIG. 3), where lysis of red blood cells can be effectuated by any of a number of methods, including the use of electric fields, and predeposited detergents, etc. In one embodiment, the lysed cells can be derivatized within the lysis microchannel with anti-$HbA_{1c}$ antibodies. Because the channel dimensions are on the order of microns, lateral diffusion of $HbA_{1c}$ can be minimized, and antibody capture can occur locally. In one embodiment, the inner walls of the lysis microchannel can be coated with a desired moiety that will be used to attached to or tag the components of the lysed cells. If desired, heating can also be used. This may be useful to speed lysis, antibody binding and/or enzyme-linked antibody reactions. In one embodiment, following an incubation time, the microchannel can be washed with buffer, for example. This buffer can come from the same elutriation buffer reservoir, or it can be from a different source.

Detection of the bound antibody can take place in an analysis chamber 20, where a simple means can be to used to detect properties of the lysed cells. For example, lysed cells of various age groupings that are labeled with a fluorescently-labeled antibody can be excited with an LED. This will allow age-segregated $HbA_{1c}$ measurement, and provide direct insight into the glucose control of the patient. In one embodiment, the labeled lysed cells can be injected into the analysis chamber a portion at a time, e.g., regions I, II, III, and IV. In the embodiment shown, the older cells (more dense and smaller cells) will be evaluated first, followed by incrementally younger cells, etc.

Figure 7:
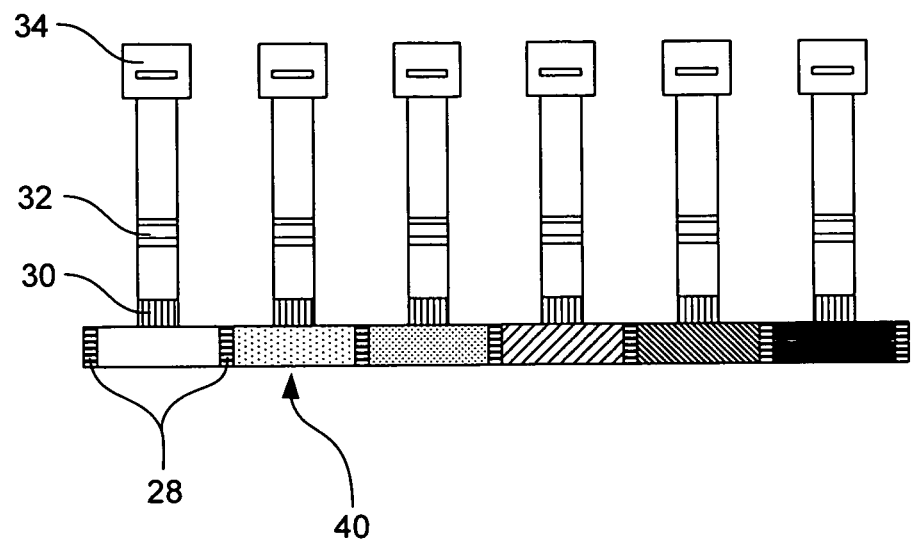
FIG. 7 is a schematic view of an alternative system in accordance with embodiments of the present invention.

Alternatively, FIG. 7 depicts another embodiment of the present invention where a gradient microchannel 40 (such as the second microchannel 18 of FIG. 3) containing gradient lysed blood cells, includes multiple resistors 28 along the gradient microchannel with associated detector regions 32 and vents 34 accessed through individual valves 30. A variety of active and passive valves can be used in the present invention as is known in the art. Specifically, an active valve that can be used includes a paraffin microactuator valve having a relatively low melting point, which creates access to the detector regions upon at least partial removal of the paraffin valve. In this embodiment, the resistors can be heated to form gas bubbles which act to at least partially isolate the groups of lysed blood cells, and further provide a motive force to move the lysed blood cells through the valves into the detector region for the $HbA_{1c}$ measurement.

Figure 8:
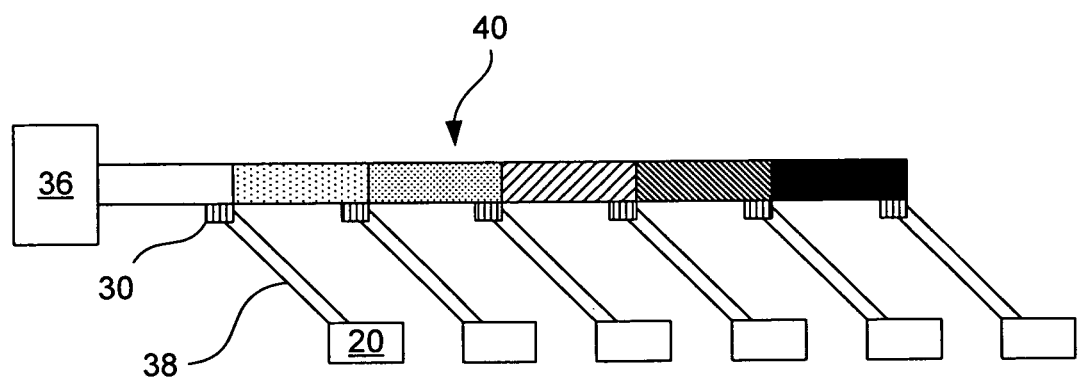
FIG. 8 is a schematic view of still another system in accordance with embodiments of the present invention.

In another embodiment, FIG. 8 depicts an alternative gradient microchannel 40 containing a gradient of blood cells. The microchannel in this embodiment is connected to a particle detector 36. Once blood cells are detected as reaching the particle detector, individual valves 30 can be opened to receive the blood cells into a corresponding lysis microchannel 38, where the blood cells can be lysed by any number of methods as described above, and corresponding $HbA_{1c}$ measurements occur at the individual detector regions 20. The lysis microchannels can be configured to receive the blood cells upon backflow of the cells, or by the use of resistors as described with respect to FIG. 7. In this embodiment, each lysis microchannel is coupled to an analysis chamber, as described previously.

It is to be understood that the above-referenced arrangements are illustrative of the application for the principles of the present invention. Numerous modifications and alternative arrangements can be devised without departing from the spirit and scope of the present invention while the present invention has been shown in the drawings and described above in connection with the exemplary embodiments(s) of the invention. It will be apparent to those of ordinary skill in the art that numerous modifications can be made without departing from the principles and concepts of the invention as set forth in the claims.

What is claimed is:

1. A method of measuring glycated hemoglobin, comprising:
   in a microfluidic device, subjecting red blood cells to counterflow centrifugation in which a combination of centrifugal force-generated fluid flow from a counterbalanced reservoir to an elutriation chamber and an opposing centrifugal force in the elutriation chamber causes the red blood cells in the chamber to form a gradient based on cellular size, the reservoir being located where a blood sample is first received in the device, and the reservoir being larger than, and in a counterbalanced position in relation to the chamber;
   collecting multiple size-specific groups of red blood cells from the centrifuged red blood cells forming the gradient based on cellular size; and
   measuring $HbA_{1c}$ levels of at least one of said groups.

2. The method of claim 1, wherein the red blood cells are from whole blood.

3. The method of claim 1, wherein after establishing the gradient, the red blood cells of the at least one of said groups are separated for measuring.

4. The method of claim 1, further comprising establishing multiple age-specific groups which includes separating red blood cells by comparing a cell age-related physical property other than cell size.

5. The method of claim 4, wherein the cell age-related property includes density, rheological properties, membrane protein ratios, dielectric properties, or electronic opacity.

6. The method of claim 4, wherein the step of establishing multiple age-specific groups includes separating red blood cells using at least one microchannel to segregate the cells.

7. The method of claim 1, wherein the step of measuring includes the preliminary step of causing cellular lysis of the red blood cells.

8. The method of claim 7, wherein the cellular lysis is caused after separating the at least one of said groups from other red blood cells.

9. The method of claim 7, wherein the cellular lysis is caused prior to separating the at least one of said groups from other red blood cells.

10. The method of claim 7, wherein the cellular lysis is caused while the red blood cells are oriented along the cellular gradient.

11. The method of claim 1, carried out, at least in part, on a microfluidic coupon.

12. The method of claim 1, wherein the microfluidic device is a microfluidic coupon that is shaped as an optical disk.

13. The method of claim 1 wherein the step of measuring includes measuring the $HbA_{1c}$ levels of two or more groups, and wherein the method further comprises comparing the measured $HbA_{1c}$ levels of the two or more groups.

14. The method of claim 1, wherein the at least one of said groups is a group including the youngest cells of the red blood cells which are below a threshold age.

15. The method of claim 1, wherein the at least one of said groups is a group including the oldest cells of the red blood cells which are above a threshold age.

16. A system for measuring glycated hemoglobin, comprising:
   a) a separating device configured to separate red blood cells into multiple size-specific groups by establishing a gradient of red blood cells using counterflow centrifugation in which a combination of a centrifugal force-generated fluid flow from a counterbalanced reservoir to an elutriation chamber and an opposing centrifugal force in the elutriation chamber causes the red blood cells in the chamber to form a gradient based on cellular size, the reservoir being located where a blood sample is first received in the device, and the reservoir being larger than, and in a counterbalanced position in relation to the chamber; and
   b) a measuring device configured to measure $HbA_{1c}$ levels of at least one of said groups.

17. The system of claim 16, wherein the red blood cells are present in a whole blood sample.

18. The system of claim 17, wherein the whole blood sample is buffered whole blood.

19. The system of claim 16, wherein the gradient is configured such that at least one of said groups is separable from other red blood cells or lysed red blood cells.

20. The system of claim 16, wherein the separating device is a microfluidic device.

21. The system of claim 16, wherein the separating device includes at least one microchannel.

22. The system of claim 16, further comprising a lysis device configured to cause lysis of the red blood cells.

23. The system of claim 16, wherein the separating device is on a microfluidic coupon.

24. The system of claim 23, wherein the microfluidic coupon is shaped as an optical disk.

25. The system of claim 16, wherein the separation device includes a system of microchannel and chamber regions configured to facilitate separating and transporting red blood cells.

26. The system of claim 25, wherein at least a portion of the system of microchannels and chambers are coated internally with a material to prevent or minimize sticking or aggregation of cells within the system.

27. The system of claim 16, wherein the system is part of a single, integrated device.

28. A system for measuring glycated hemoglobin, comprising:
   a) means for separating red blood cells into multiple size-specific groups by establishing a gradient of red blood cells using counterflow centrifugation in which a combination of a centrifugal force-generated fluid flow from a counterbalanced reservoir to an elutriation chamber and an opposing centrifugal force in the elutriation chamber causes the red blood cells in the chamber to form a gradient based on cellular size, the reservoir being located where a blood sample is first received in the device, and the reservoir being larger than, and in a counterbalanced position in relation to the chamber; and
   b) means for measuring $HbA_{1c}$ levels of at least one of said groups by competitive or immunometric assays.

29. The system of claim 28, wherein the red blood cells are present in a whole blood sample.

30. The system of claim 29, wherein the whole blood sample is buffered whole blood.

* * * * *